United States Patent
Schwarz et al.

(10) Patent No.: US 6,884,893 B1
(45) Date of Patent: Apr. 26, 2005

(54) METHOD FOR SELECTIVELY DISSOCIATING CYCLIC CARBOXYLIC ACID ANHYDRIDES

(75) Inventors: Michael Schwarz, Weiterstadt (DE); Jürgen Eckstein, Rossdorf (DE)

(73) Assignee: MERCK Patent GmbH, Darmstadt (DE)

( * ) Notice: Subject to any disclaimer, the term of this patent is extended or adjusted under 35 U.S.C. 154(b) by 0 days.

(21) Appl. No.: 10/110,068
(22) PCT Filed: Oct. 2, 2000
(86) PCT No.: PCT/EP00/09636
   § 371 (c)(1),
   (2), (4) Date: Apr. 8, 2002
(87) PCT Pub. No.: WO01/25215
   PCT Pub. Date: Apr. 12, 2001

(30) Foreign Application Priority Data

Oct. 6, 1999 (DE) .......................... 199 47 953

(51) Int. Cl.$^7$ ............................................. C07D 405/02
(52) U.S. Cl. .................. 548/303.1; 548/322.5
(58) Field of Search ............................ 548/303.1, 322.5

(56) References Cited

FOREIGN PATENT DOCUMENTS

EP         044158         1/1982

OTHER PUBLICATIONS

Patent Abstracts of Japan vol. 7, No. 143 & JP 58055464.

*Primary Examiner*—Taofiq Solola
(74) *Attorney, Agent, or Firm*—Millen White Zelano & Branigan P.C.

(57) ABSTRACT

The invention relates to a method for selectively dissociating cyclic carboxylic acid anhydrides. According to the inventive method, a chiral amino alcohol with a tertiary amino group that may have a partially or completely bridged structure is used as the chiral auxiliary reagent.

12 Claims, No Drawings

METHOD FOR SELECTIVELY DISSOCIATING CYCLIC CARBOXYLIC ACID ANHYDRIDES

This application is a 371 of PCT/EP00/09636 filed Oct. 2, 2000.

The present invention relates to a novel process for the selective opening of cyclic carboxylic anhydrides, in particular of (4S,5R)-1,3-dibenzyl-1H-furo[3,4-d]imidazole-2,4,6-trione, an intermediate in the synthesis of biotin.

A very important intermediate step in the synthesis of biotin is opening of the 'anhydride' (4S,5R)-1,3-dibenzyl-1H-furo[3,4-d]imidazole-2,4,6-trione using alcohol to give the racemic monoester.

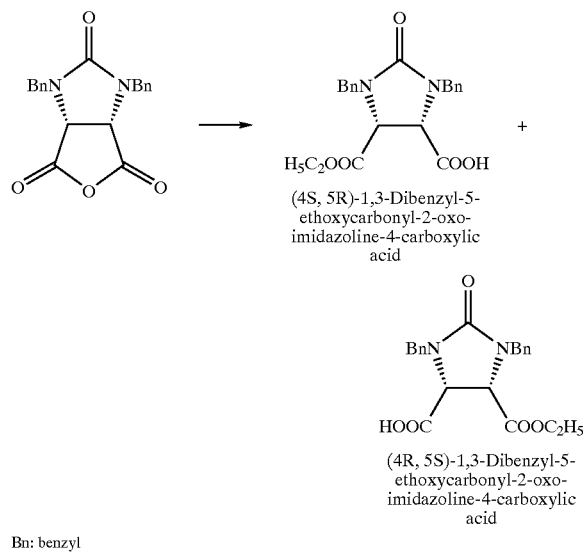

(4S, 5R)-1,3-Dibenzyl-5-ethoxycarbonyl-2-oxo-imidazoline-4-carboxylic acid (4R, 5S)-1,3-Dibenzyl-5-ethoxycarbonyl-2-oxo-imidazoline-4-carboxylic acid Bn: benzyl The desired monoester [(4S,5R)-1,3-dibenzyl-5-ethoxycarbonyl-2-oxo-imidazoline-4-carboxylic acid] is isolated from the mixture of the enantiomers by resolving the racemate using ephedrine. The ester function is subsequently reduced to the hydroxymethyl group using boron hydride, and the ring is closed under acidic conditions to give the 'lactone' (3aS,6aR)-1,3-dibenzyldihydro-1H-furo [3,4-d]imidazole-2,4-dione. This optically active lactone is—as already mentioned—a known and valuable intermediate in the synthesis of (+)-biotin and of derivatives and related compounds thereof.

The undesired enantiomer is returned into the synthesis cycle by saponification of the ester group and conversion of the dicarboxylic acid into the 'anhydride'.

The throughput of this synthesis sequence can be considerably improved if the reaction of the 'anhydride' with the reagent proceeds selectively, i.e. one of the two possible products is formed preferentially. Given correspondingly high selectivity, recycling of the undesired ring-opening product is no longer necessary, which means that the processing duration of the reaction becomes significantly shorter.

Corresponding processes are already known from the patent literature. Thus, for example, Hoffmann-La Roche describe in EP 0 161 580 the reaction of the 'anhydride' with chiral secondary alcohols of the CH₃CH(OH)R type in tetrahydrofuran. The (4S,5R)-monoester is preferentially formed here, and can—as described above—be reacted further to give the 'lactone'.

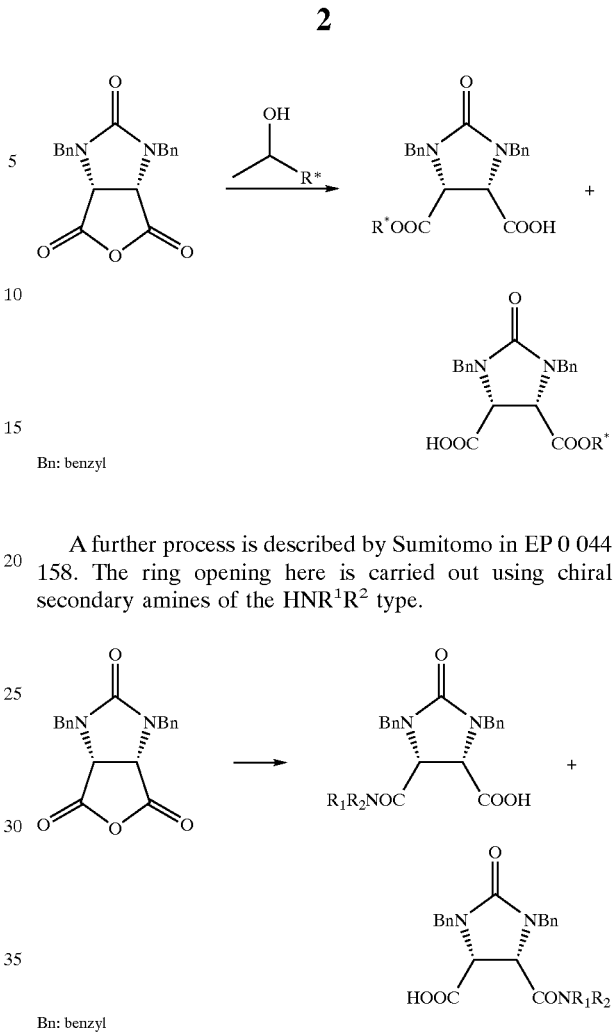

Bn: benzyl

A further process is described by Sumitomo in EP 0 044 158. The ring opening here is carried out using chiral secondary amines of the $HNR^1R^2$ type.

Bn: benzyl

For conversion into the 'lactone', the free carboxylic acid group of the intermediate compound must firstly be esterified using an alcohol before the 'lactone' can be obtained by reduction using boron hydrides followed by acidic cyclisation.

Both processes have specific disadvantages: in the Hoffmann-La Roche process, the 'lactone' reaction product and the chiral auxiliary reagent are both in the organic phase after completion of the lactone synthesis and have to be separated from one another.

This problem does not occur in the Sumitomo process. Since the chiral auxiliary reagent is an amine, it is protonated during the acidic cyclisation and, after work-up, is found in the water phase, while the 'lactone' is separated off in the organic phase. Rather, the disadvantage of the process consists in the necessity that the free carboxylic acid has to be esterified in an additional step. In addition, an amide bond is more difficult to break than an ester bond, which means that more drastic conditions have to be employed in the acidic cyclisation to give the 'lactone', which can result in increased formation of by-products.

There thus continues to be a demand for a process for the selective cleavage of this anhydride which is simple and effective to carry out and which gives the desired ring-opening product in good yields with high optical purity.

Surprisingly, it has now been found that on use of substituted 2-amino-alcohols containing a tertiary amino group in a suitable solvent, very high selectivity for a ring-opening product can be achieved. In principle, all compounds which contain a primary, secondary or tertiary alcohol function and a tertiary amino group are suitable for the process according to the invention.

The invention therefore relates to a process for the selective cleavage of cycloanhydrides of the formula I

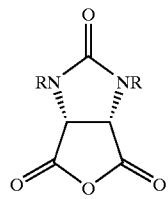

(I)

in which

R is benzyl, alkyl having from 1 to 6 carbon atoms or aryl, to give the corresponding monoesters, characterised in that the compound of the formula I is reacted a) with a chiral aminoalcohol of the general formula II

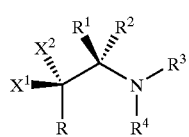

(II)

in which $X^1$ and $X^2$ are each R or OH, with the proviso that $X^1$ is not the same as $X^2$, and one of the two radicals is OH, R, $R^1$ and $R^2$ are each H, alkyl having 1–12 carbon atoms, unsubstituted or substituted cycloalkyl having 3–8 carbon atoms, alkenyl, aryl, arylalkyl, heteroaryl, heteroarylalkyl and condensed systems, and R and $R^1$ or R and $R^2$ together are alternatively unsubstituted or substituted cycloalkyl having 5–8 carbon atoms, in which, in addition, one or two O, N and/or S atoms may be present, and which may also be in partially or fully unsaturated form, and where the substituents may be alkyl, alkenyl, alkoxy, aryl, aryloxy, dialkylamine or aprotic radicals in general, with the proviso that at least one of the radicals R, $R^1$ and $R^2$ is an unsubstituted or substituted cycloalkyl, alkenyl, heteroaryl, heteroarylalkyl or a condensed system, or R and $R^1$ or R and $R^2$ together are alternatively unsubstituted or substituted cycloalkyl having 5–8 carbon atoms, as described above,

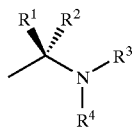

is not a partially or fully linked structure described below, $R^3$ and $R^4$ are each alkyl having 1–12 carbon atoms, unsubstituted or substituted cycloalkyl having 3–8 carbon atoms, alkenyl, aryl, arylalkyl, heteroaryl, heteroarylalkyl and condensed systems, with the possible substituents described for R, and

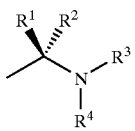

may be a partially or fully linked structure, which may be substituted and in which the substituents may be alkyl, alkoxy, alkenyl, aryl, aryloxy, dialkylamino and other aprotic radicals, in an inert solvent, or b) with a chiral aminoalcohol of the general formula III

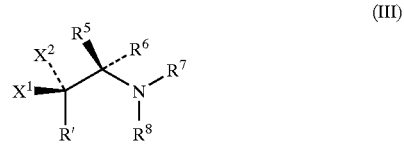

(III)

in which $X^1$ and $X^2$ are each R' or OH, with the proviso that $X^1$ is not the same as $X^2$, and one of the two radicals is OH, R', $R^5$ and $R^6$ are each H, alkyl having 1–12 carbon atoms or aryl, which may be substituted by alkyl or alkoxy, and $R^7$ and $R^8$ are each alkyl having 1–12 carbon atoms or aryl, which may be substituted by alkyl or alkoxy, in toluene, benzene or xylene at temperatures of from 15° to 35° C., in high selectivity to give a diastereomer, and the monoester is, if desired, subsequently reduced using boron hydride, and the ring is then closed to give the corresponding lactone.

If $X^1$ or $X^2$ is R or R', the two radicals $X^1$ and R or $X^2$ and R or $X^1$ and R' or $X^2$ and R' can have different meanings.

In the formulae above and below, alkyl is in each case straight-chain or branched alkyl having from 1 to 12 carbon atoms, preferably having from 1 to 8 carbon atoms, and is accordingly preferably methyl, ethyl, propyl, isopropyl, butyl, isobutyl, tert-butyl, pentyl, hexyl, heptyl or alternatively octyl. Alkyl in the formulae above and below is particularly preferably in each case straight-chain or branched alkyl having from 1 to 4 carbon atoms.

Cycloalkyl is cyclopropyl, cyclobutyl, cyclopentyl, cyclohexyl, cycloheptyl or alternatively cyclooctyl, each of which may also be in substituted form.

Suitable substituents in the groups above and below are preferably alkyl, alkoxy, alkenyl, aryl or aryloxy, dialkylamino and other aprotic radicals. Particular preference is given here to substituents such as methyl, ethyl, methoxy, ethoxy, ethenyl, propenyl, phenyl, phenoxy, dimethylamino or alternatively diethylamino.

Alkenyl is preferably ethenyl, propenyl, butenyl or pentenyl, aryl is preferably phenyl, and arylalkyl is preferably benzyl or phenethyl.

Heteroaryl is preferably pyridinyl, pyrimidinyl and similar rings containing heteroatoms, heteroarylalkyl is consequently then pyridinylmethyl, pyrimidinylmethyl and the like.

Possible condensed systems are preferably the naphthyl, biphenyl or quinolinyl radicals or alternatively cinnolinyl and similar systems.

All these groups may be in unsubstituted or substituted form, with suitable substituents preferably being the radicals described above.

R in the formula II is preferably aryl, heteroaryl and condensed aromatic radicals, if desired with substituents, such as alkyl, alkenyl, alkoxy, aryl, aryloxy or dialkylamino.

$R^1$ and $R^2$ are preferably H or straight-chain alkyl having from 1 to 4 carbon atoms.

$R^3$ and $R^4$ are likewise preferably the groups mentioned for R, $R^1$ and $R^2$, but not H.

Also suitable for the process according to the invention are, for example, chiral auxiliaries in which R and $R^1$ or R and $R^2$ together are alternatively unsubstituted or substituted cycloalkyl having 5–8 carbon atoms, preferably having 6–8 carbon atoms, and in particular have the meaning cyclohexyl.

It is also possible for one or two, preferably non-adjacent $CH_2$ groups in these cycloalkyl groups to be replaced by O, S and/or N atoms, and to be, for example, piperidinyl or dioxanyl. These cycloalkyl groups may furthermore also be in partially or fully unsaturated form, i.e. may be, for example, cyclohexenyl.

Also suitable for the process according to the invention are, for example, chiral auxiliaries in which two or more, preferably 2 or 3, of the radicals $R^1$ to $R^4$ are linked to one another. Examples of chiral auxiliaries of this type are compounds in which the radical

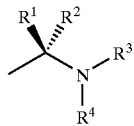

has the following meanings:

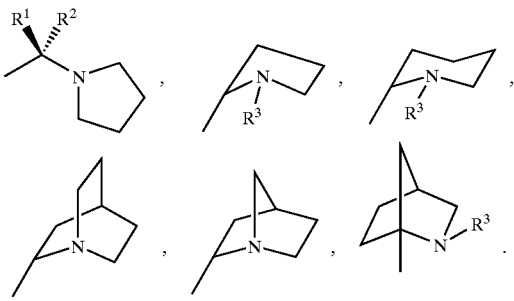

$R^1$ and $R^2$ are as defined above. $R^3$ here is preferably alkyl or alkenyl, in particular having up to 4 carbon atoms.

However, further substituents are also possible elsewhere in the ring systems. Suitable substituents in the ring systems are preferably alkyl, alkoxy, alkenyl, aryl, aryloxy, dialkylamino and other aprotic radicals. Particular preference is given here to substituents such as methyl, ethyl, methoxy, ethoxy, ethenyl, propenyl, phenyl, phenoxy, dimethylamino or alternatively diethylamino.

If the radical

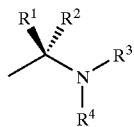

is a partially or fully linked structure, the other radicals preferably have the following meaning:

R is aryl, heteroaryl and condensed aromatic radicals, where these groups may also be substituted by alkyl, alkenyl, alkoxy, aryloxy, dialkylamino and aprotic radicals in general, $R^1$ and $R^2$ are each H or alkyl having 14 carbon atoms,
$R^3$ and $R^4$ are each alkyl having 14 carbon atoms, and
R and $R^1$ or R and $R^2$ together are alternatively unsubstituted or substituted cycloalkyl having 5–8 carbon atoms, in which, in addition, one or two O, N and/or S atoms may be present, and which may also be in partially or fully unsaturated form, and where the substituents may be alkyl, alkenyl, alkoxy, aryl, aryloxy, dialkylamine or aprotic radicals in general.

If the radical

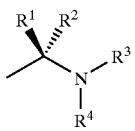

is not a partially or fully linked structure described above, the proviso exists that then at least one of the radicals R, $R^1$ and $R^2$ is an unsubstituted or substituted cycloalkyl, alkenyl, heteroaryl, heteroarylalkyl or a condensed system, or R and $R^1$ or R and $R^2$ together are alternatively unsubstituted or substituted cycloalkyl having 5–8 carbon atoms, as described above. If this proviso is not satisfied, then the substances fall under the formula III.

In the formula III, R', $R^5$ and $R^6$ are each preferably H, alkyl having 1–4 carbon atoms or aryl, which may be substituted by alkyl or alkoxy, and $R^7$ and $R^8$ are each preferably alkyl having 14 carbon atoms or aryl, which may be substituted by alkyl or alkoxy.

Accordingly, R', $R^5$ and $R^6$ are particularly preferably methyl, ethyl, propyl, isopropyl or butyl, phenyl, benzyl, tolyl or methoxyphenyl.

The process according to the invention is carried out with the chiral auxiliary reagents of the formula II, preferably in an inert solvent, at temperatures between 0° C. and the boiling point of the solvent used, particularly preferably between 20° and 50° C.

Suitable solvents here are all known, inert solvents. Preference is given to solvents such as benzene, toluene, xylene, ethylbenzene, tetrahydrofuran, dioxane or other ethers, methylene chloride, chloroform or alternatively ethyl acetate. Particular preference is given to the solvents toluene, benzene or tetrahydrofuran.

With respect to the auxiliary reagents of the formula III, it has been found, surprisingly, that higher selectivity of one diastereomer can be achieved using these compounds if the process here is carried out in toluene, benzene or xylene at temperatures between 15° and 35° C.

The Japanese patent application JP 58055464 discloses the use of the chiral aminoalcohols of the formula III for the preparation of optically active 2-oxoimidazolidine derivatives (by ring opening of a carboxylic anhydride). However, the process described in this invention in variant b) represents a selection invention with respect to this document.

As is evident from the examples in the Japanese application, the reaction is carried out in tetrahydrofuran, preferably at the lowest possible temperatures (around the freezing point or below). The two starting materials here are introduced into the apparatus, and THF as solvent is added at 4° C., the chiral auxiliary reagent used is (1R,2S)-2-dimethylamino-1-phenylpropanol. The mixture is then cooled to −4° C., and the reaction is continued at this temperature for about 16 hours. The desired monoester is obtained in an optical purity of only 61% ee.

In the present invention, however, it has surprisingly been found that performance of the reaction at elevated temperatures and in the solvents toluene, benzene or xylene produces significantly better differentiation of, for example, 91:9 in favour of the desired diastereomeric product and respectively an optical purity of 82% ee of the synthesised monoester (cf. in this respect Example 2B).

This optimised procedure is not revealed by the description in the Japanese application.

In both variants of the process according to the invention, the corresponding anhydride is suspended or dissolved in the solvent, and the chiral auxiliary reagent, dissolved in the same solvent, is subsequently added slowly. Reaction times vary between 2 hours and 3 days, preferably between 2 and 20 hours.

Suitable ratios of chiral auxiliary reagent to starting material are between 0.9 and 1.5 equivalents of auxiliary reagent. Preferred ratios are between 1.0 and 1.2 equivalents.

Particularly preferred chiral auxiliaries for the process according to the invention are selected from the following compounds:
(+)-(1S,2R)-2-dimethylamino-1-phenyl-1-propanol or alternatively (+)-N-methylephedrine, (−)-N-methylephedrine, (1R,2S)(−)-2-(N,N-di-n-butyl)-amino-1-phenyl-1-propanol, and (−)-quinine and (−)-cinchonidine having the following formulae:

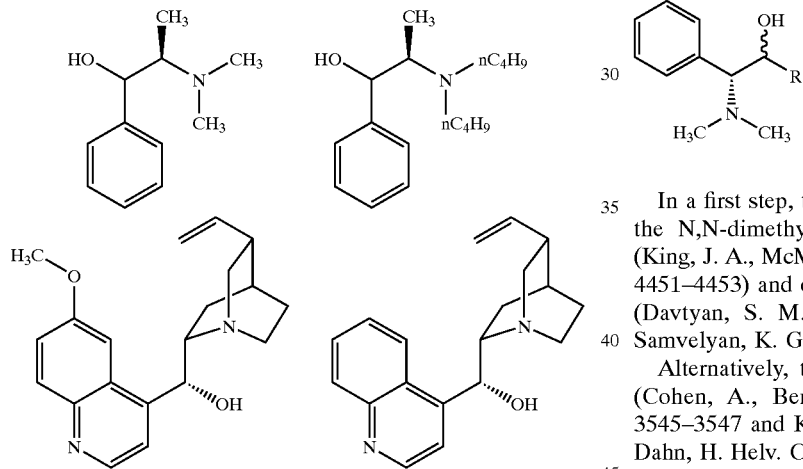

Also suitable are (2S)-(−)-2-hydroxymethyl-1-methylpyrrolidine, (+)-cinchonine or 1-hydroxy-2-pyrrolidinocyclohexane, furthermore also (+)-quinidine.

The chiral auxiliary reagents of the formula II or III can also be prepared, for example, from natural or unnatural amino acids.

Synthetic scheme 1 below describes the possible reactions using the example of (1R)-(−)-1-amino-1-phenylacetic acid [D-phenylglycine], without this being intended to represent a restriction to this specific amino acid.

Scheme 1

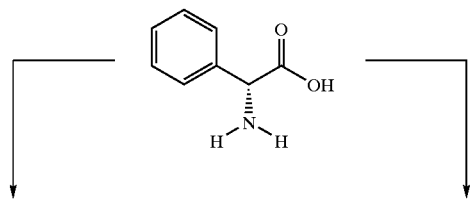

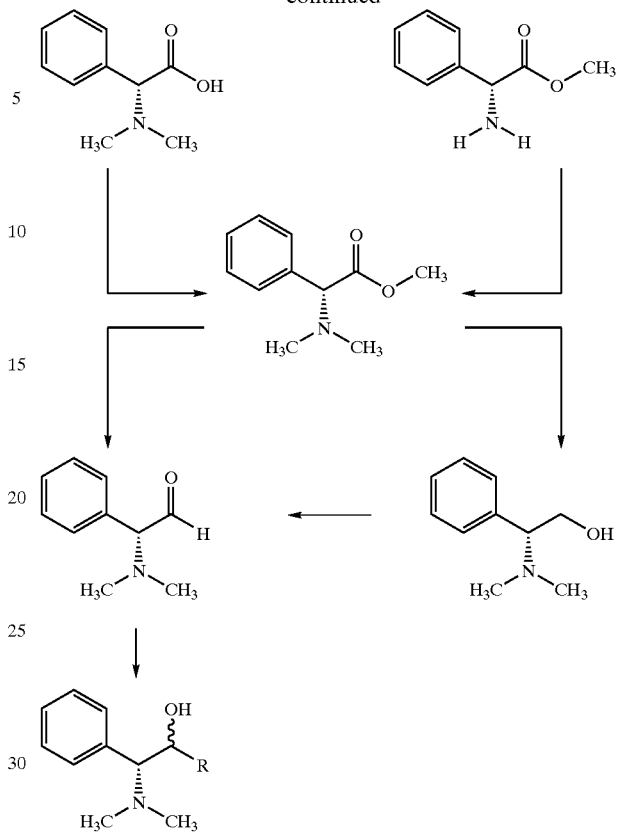

In a first step, the free amino acid can be converted into the N,N-dimethyl compound using formaldehyde/H$_2$/Pt (King, J. A., McMillan, F. H. J. Am. Chem. Soc. 1951, 73, 4451–4453) and esterified in alcohols with acidic catalysis (Davtyan, S. M.; Papayan, G. L.; Chachoyan, A. M.; Samvelyan, K. G. Pharm. Chem. J. 1982, 16, 517).

Alternatively, the esterification can be carried out first (Cohen, A., Bergmann, E. D. Tetrahedron 1966, 22, 3545–3547 and Klyne, W.; Scopes, P. M.; Thomas, R. N.; Dahn, H. Helv. Chim. Acta 1971, 54, 2420–2430), and the reductive alkylation can be carried out using formaldehyde/H$_2$/Pd (Bowman, R. E.; Stroud, H. H. J. Chem. Soc. 1950, 1342–1345) or higher alkanals (Bowman, R. E. J. Chem. Soc. 1950, 1346–1349).

The scheme does not show the possibility of reducing amino acids to 2-aminoethanols using NaBH$_4$ (Abiko, A.; Masamune, S. Tetrahedron Lett. 1992, 33, 5517–5518) or LiAlH$_4$ (Dieter, R. K.; Deo, N.; Lagu, B.; Dieter, J. W. J. Org. Chem. 1992, 57, 1663–1671) and then subjecting these compounds to reductive alkylation (Dieter, R. K.; Deo, N.; Lagu, B.; Dieter, J. W. J. Org. Chem. 1992, 57, 1663–1671).

An alternative alkylation using ω-halocarboxylic acid chlorides (Okawara, T.; Matsuda, T.; Noguchi, Y.; Furukawa, M. Chem. Pharm. Bull. 1982, 30, 1574–1578) gives pyrrolidinyl- or piperidinylamino acids.

The N,N-dialkylamino acid ester can be converted into N,N-dialkylaminoaldehydes by partial reduction using DiBAlH (Dondoni, A.; Perrone, D.; Merino, P. J. Org. Chem. 1995, 60, 8074–8080) or complete reduction using LiAlH$_4$ and Swern oxidation (Génisson, Y.; Mehmandoust, M.; Marazano, C.; Das, B. C. Heterocycles 1994, 39, 811–818) of the resultant alcohol.

The N,N-dialkylaminoaldehydes can be converted into syn-substituted aminoalcohols using dialkylzinc (Andrés, J. M.; Barrio, R.; Martinez, M. A.; Pedrosa, R.; Pérez-Encabo, A. J. Org. Chem. 1996, 61, 4210). Other organometallic reagents preferentially give the anti-configuration.

In the process according to the invention, the resultant mixture of the diastereomeric monoesters can be checked for selectivity by HPLC. The monoesters do not first have to be isolated, but instead can, if desired, immediately be processed further in situ by reduction of the ester function and cyclisation to the 'lactone'. Here too, the purity can then be checked by HPLC in a chiral column by known methods. It is also demonstrated thereby that the chiral information is, as expected, passed on in the conversions into the 'lactone'.

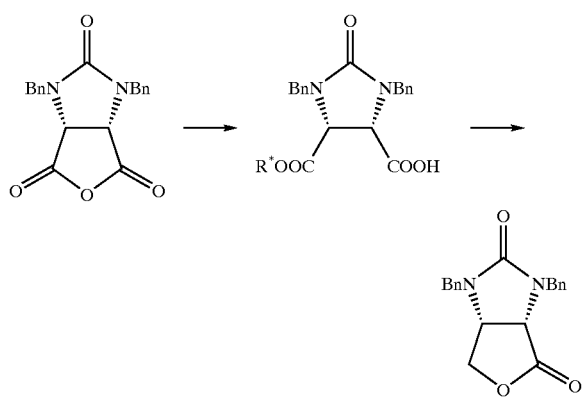

Bn: benzyl

The above-mentioned disadvantages of the competing processes can be avoided by means of the chiral auxiliary reagents according to the invention. The combination present in the said structures of, preferably, a primary or secondary alcohol function and a tertiary amino group only facilitates the formation of an ester bond in the reaction with the 'anhydride'. However, the amino group can be protonated, and it can consequently be assumed that the monoester is in the form of an internal salt. In formal terms, the ester bond is cleaved by the reduction using boron hydride, and the chiral auxiliary reagent is liberated in unchanged form. Under the conditions of the acidic cyclisation to the 'lactone', the chiral auxiliary reagent is protonated and transferred into the water phase during work-up. In this way, simple separation and recovery of the auxiliary is possible.

The solvents which are suitable for the process according to the invention are dependent on the reagent selected, as is also described in the different variants a) and b) of the process. For example, the (1R,2S)-N,N-dialkylephedrines give significantly better results in toluene than in THF. The reactions with (−)-quinine proceed with approximately comparable results both in THF and in toluene.

It can be seen from the examples that the desired products can be obtained in high selectivity. A ratio of the two monoesters to one another which is greater than 70:30 is always obtained.

With the process variants according to the invention that are described here, simple and effective methods for the selective ring opening of cyclocarboxylic anhydrides, in particular for the opening of (4S,5R)-1,3-dibenzyl-1H-furo[3,4-d]imidazole-2,4,6-trione to give a desired monoester as part of the synthesis of biotin, are now available.

The use of the process according to the invention for the above-described selective cleavage of (4S,5R)-1,3-dibenzyl-1H-furo[3,4-d]imidazole-2,4,6-trione is likewise a subject-matter of the invention.

Even without further comments, it is assumed that a person skilled in the art will be able to utilise the above description in the broadest scope. The preferred embodiments should therefore merely be regarded as descriptive disclosure which is absolutely not limiting in any way.

The full disclosure content of all applications and publications listed above and below are incorporated into this application by way of reference.

Examples which are intended to illustrate the invention without representing a limitation are given below.

EXAMPLES

In each of the following examples, the anhydride (4S, 5R)-1,3-dibenzyl-1H-furo[3,4-d]imidazole-2,4,6-trione is employed.

The following compounds were investigated as examples of the chiral auxiliary reagents for the process according to the invention:

| No. | Name | Structure |
|---|---|---|
| 1 | (+)-N-Methylephedrine (+)-(1S, 2R)-2-Dimethyl-amino-1-phenyl-1-propanol | 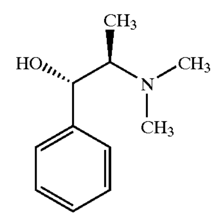 |
| 2 | (−)-N-Methylephedrine (−)-(1R, 2S)-2-Dimethyl-amino-1-phenyl-1-propanol | 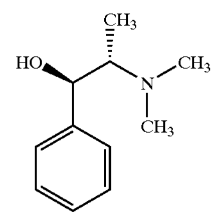 |
| 3 | (−)-Quinine 6′-Methoxycinchonan-6-ol | 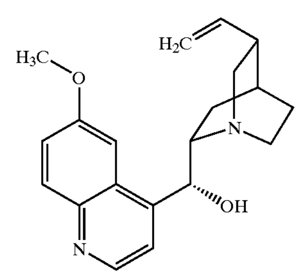 |
| 4 | (1S, 2R)-(−)-(N,N-Di-n-butylamino)-1-phenyl-1-propanol | 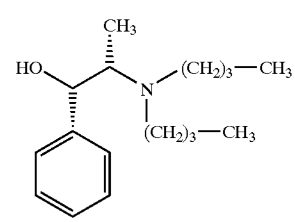 |

-continued

| No. | Name | Structure |
|---|---|---|
| 5 | (+)-Cinchonine | 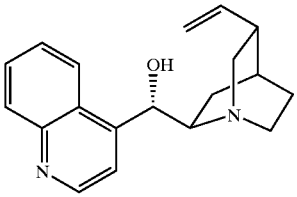 |
| 6 | (−)-Cinchonidine | 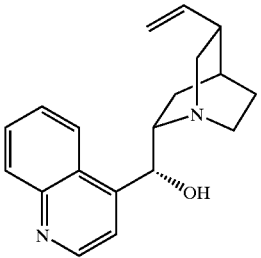 |
| 7 | trans-1-Hydroxy-2-pyrrolidinocyclohexane | 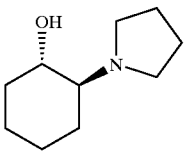 |

Example 1
(1S,2R)-(+)-2-Dimethylamino-1-phenyl-1-propanol
As Chiral Auxiliary Reagent 5 g (14.865 mmol) of anhydride are suspended in 50 g of toluene. A solution of 3.0 g (16.4 mmol; 110 mol %) of (+)-N-methylephedrine in 19 g of toluene is added dropwise at 24°–29° C. over the course of 35 minutes. After the mixture has been stirred at RT for a further 4 hours, the reaction solution is evaporated in a rotary evaporator, and the residue is chromatographed over 150 g of silica gel with dichloromethane/methanol 85:15.

(4S,5R)- to (4R,5S)-monoester 9:91 (HPLC)
Yield: 7.0 g (91%)

The solution of the product in 20 g of THF is added dropwise to a suspension of 1.52 g (38.6 mmol; 300 mol %) of sodium borohydride in 30 g of THF, and the reaction is subsequently warmed to 63°–65° C. in 35 minutes and stirred for 180 minutes. The batch is then evaporated in a rotary evaporator, the residue is taken up in 80 ml of methanol, and 10.7 ml of 37% HCl are added. The reaction is warmed to 62°–64° C. in 30 minutes, stirred at this temperature for a further 100 minutes and stirred for a further 14 hours with cooling to room temperature [RT]. The reaction solution is evaporated in a rotary evaporator, and the residue is partitioned between 100 g of demineralised water and 100 g of toluene. The organic extracts are evaporated in a rotary evaporator, and the residue is chromatographed over 350 g of silica gel with toluene/ethyl acetate 7:3.

Yield: 1.96 g (47%)
Optical rotation $[\alpha]_{325}^{20}$=143.5° (c=1 in benzene). (3aS, 6aR)- to (3aR,6aS)-lactone=11:89 (HPLC)

Comparative Example to Example 1—Solvent THF 5 g (14.865 mmol) of anhydride are suspended in 40 g of tetrahydrofuran [THF] in a preheated four-necked flask and dissolved with stirring. A solution of 3.54 g (19.34 mmol; 130 mol %) of (1S,2R)-(+)-2-dimethylamino-1-phenyl-1-propanol [(+)-N-methylephedrine] in 14 g of THF is added dropwise over the course of 7 minutes. After the mixture has been stirred at 64° C. for 20 hours, a solution of 1.9 g (10.4 mmol; 70 mol %) of (+)-N-methylephedrine in 15 g of THF is added dropwise, and the mixture is stirred at this temperature for a further 6 hours. The reaction solution is cooled and evaporated to dryness in a rotary evaporator. The residue is dissolved in dichloromethane/methanol 85:15, and this mixture is chromatographed over 200 g of silica gel. The product-containing fractions are evaporated to dryness.

The ratio of (4S,5R)- to (4R,5S)-monoester was determined as 40:60 by HPLC (RP-18(e) 250–4, 1 ml/min acetonitrile:water:NaH$_2$PO$_4$ buffer).

Yield: 6.7 g (87.5%)

The solution of the product in 20 g of THF is added dropwise to a suspension of 1.46 g (37 mmol; 300 mol %) of sodium borohydride in 30 g of THF, and the reaction is subsequently warmed to 620–64° C. in 30 minutes and stirred for 90 minutes. The batch is then evaporated in a rotary evaporator, the residue is taken up in 80 ml of methanol, and 10.2 ml of 37% HCl are added. The reaction is warmed to 62°–64° C. in 20 minutes, stirred at this temperature for a further 70 minutes and stirred for a further 14 hours with cooling to room temperature [RT]. The reaction solution is evaporated in a rotary evaporator, and the residue is partitioned between 100 g of demineralised water and 50 g of toluene. The organic extracts are evaporated in a rotary evaporator, and the residue is chromatographed over 150 g of silica gel with toluene/ethyl acetate 7:3.

Yield: 0.6 g (14%)
Optical rotation $[\alpha]_{365}^{20}$=−19.2° (c=1 in benzene). (3aS, 6aR)- to (3aR,6aS)-lactone=45:55 (HPLC)

Example 2
(1R,2S)-(−)-2-Dimethylamino-1-phenyl-1-propanol
As Chiral Auxiliary Reagent Example 2A—Solvent Benzene 5 g (14.865 mmol) of anhydride are suspended in 50 g of benzene. A solution of 2.86 g (15.6 mmol; 105 mol %) of (−)-N-methylephedrine in 16 g of benzene is added dropwise at 24°–27° C. over the course of 1.5 hours. After the mixture has been stirred at RT for a further 16 hours, the reaction 61 solution is evaporated in a rotary evaporator.

(4S,5R)- to (4R,5S)-monoester=89:11 (HPLC)

The solution of the crude product in 30 g of THF and 2.47 g of methanol is added dropwise at 63°–64° C. over the course of 125 minutes to a suspension of 1.52 g (38.6 mmol; 261 mol %) of sodium borohydride in 20 g of THF, and the reaction solution is stirred for a further 3 hours in total. The reaction solution is concentrated in a rotary evaporator, added dropwise at about 57° C. to 36 g of demineralised water, and 9.54 ml of 37% HCl are added. The two-phase mixture is stirred at about 62° C. for 75 minutes and subsequently for 16 hours with cooling to RT. The residual THF is stripped off in a rotary evaporator, 50 g of toluene are added, and the pH is adjusted to pH 6.5–7 using about 8 ml of 32% NaOH. The phases are separated, the aqueous phase is post-extracted with 20 ml of toluene, and the organic extracts are evaporated in a rotary evaporator. The residue is chromatographed over 250 g of silica gel with toluene/ethyl acetate 7:3.

Yield: 3.2 g (67.6%)
(3aS,6aR)- to (3aR,6aS)-lactone=89:11 (HPLC)

Example 2B1—Solvent Toluene 5 g (14.865 mmol) of anhydride are suspended in 50 g of toluene. A solution of 2.86 g (15.6 mmol; 105 mol %) of (1R,2S)-(−)-2-dimethylamino-1-phenyl-1-propanol [(−)-N-methylephedrine] in 19 g of toluene is added dropwise at 24°–26° C. over the course of 95 minutes. After the mixture has been stirred at RT for a further 16 hours, the reaction solution is evaporated in a rotary evaporator. The solution of the crude product in 20 g of THF is added dropwise to a suspension of 1.65 g (41.9 mmol; 300 mol %) of sodium borohydride in 30 THF, 0.91 g of methanol is subsequently added over the course of 3 minutes, the reaction is warmed to 63°–65° C. in 35 minutes and stirred for a further 3 hours in total. The batch is then evaporated in a rotary evaporator, the residue is taken up in 80 ml of methanol, and 11.7 ml of 37% HCl are added. The reaction is warmed to 62°–64° C. in 25 minutes and stirred for a further 40 minutes. The reaction solution is evaporated in a rotary evaporator, and the residue is partitioned between 50 g of demineralised water, 8 ml of 32% NaOH solution and 100 g of toluene (pH 6.5–7). The aqueous phase is post-extracted with 20 ml of toluene, and the organic extracts are evaporated in a rotary evaporator. The residue is chromatographed over 350 g of silica gel with toluene/ethyl acetate 7:3. Yield: 2.8 g (62%)

Optical rotation $[\alpha]_{365}^{20}$=+160.90° (c=1 in benzene). (3aS,6aR)- to (3aR,6aS)-lactone=91:9 (HPLC)

Example 2B2—Solvent Toluene 80.6 g (237.84 mmol) of anhydride are suspended in 172 g of toluene. 43.5 g (237.81 mmol; 100 mol %) of (1R,2S)-(−)-2-dimethylamino-1-phenyl-1-propanol dissolved in 300 g of toluene are added at 24° C.–27° C. over the course of 8.5 hours. After the mixture has been stirred at RT for a further 10 minutes, a sample of the reaction solution is analysed by HPLC.

Conversion: 97.5%

(4S,5R)- to (4R,5S)-monoester=89:11 (HPLC).

After addition of seed crystals (1 g suspended in 4 g of toluene), the reaction is stirred overnight. The crystals are isolated, rinsed with 80 g of toluene and dried at 35° C. in a vacuum drying cabinet.

Yield: 102.8 g (84%)

(4S,5R)- to (4R,5S)-monoester=99.3:0.7 (HPLC).

A solution of 51 g (98.9 mmol) of crystallised monoester in 16 g of methanol and 200 g of tetrahydrofuran is added over the course of 50 minutes to 6.8 g (296.6 mmol; 300 mol %) of lithium borohydride in 135 g of THF. After a reaction time of 95 minutes, the reaction solution is concentrated, the residue is taken up in 240 g of water, and 66 ml of 37% aqueous HCl solution are added. The emulsion is stirred at a reaction temperature of 70° C. for 2 hours. The residual THF is subsequently distilled off, the water phase is adjusted to pH 55.5 using 38 ml of 32% sodium hydroxide solution, and 200 g of toluene are added. After phase separation, the organic fraction is evaporated to dryness. The crude product (30 g) obtained in this way is recrystallised from 75 g of toluene.

Yield: 25.2 g (79%)

Content: 99.9% (HPLC)

A solution of 51 g (98.9 mmol) of crystallised monoester in 4 g of methanol, 31 g of trimethyl borate and 150 g of tetrahydrofuran is added over the course of 95 minutes to 10.4 g (263.9 mmol; 267 mol %) of sodium borohydride in 135 g of THF. After a reaction time of 18 hours, the reaction solution is concentrated, the residue is taken up in 240 g of water, and 66 ml of 37% aqueous HCl solution are added. The emulsion is stirred at a reaction temperature of 66° C. for 2 hours. The residual THF is subsequently distilled off, the water phase is adjusted to pH 6.5 using 45 ml of 32% sodium hydroxide solution, and 200 g of toluene are added. After phase separation, the organic fraction is evaporated to dryness. The crude product (29 g) obtained in this way is recrystallised from 52 g of toluene.

Yield: 22.8 g (71%)

Content: 99.9% (HPLC)

Example 2C—Solvent Xylene 5 g (14.865 mmol) of anhydride are suspended in 55 g of xylene. A solution of 2.86 g (15.6 mmol; 105 mol %) of (−)-N-methylephedrine in 24 g of xylene is added dropwise at 24°–27° C. over the course of 110 minutes. After the mixture has been stirred at RT for a further 65 hours, the reaction solution is evaporated in a rotary evaporator.

(4S,5R)- to (4R,5S)-monoester=82:18 (HPLC)

The solution of the crude product in 30 g of THF and 0.99 g of methanol is added dropwise at 63°–64° C. over the course of 2 hours to a suspension of 1.52 g (38.6 mmol; 261 mol %) of sodium borohydride in 20 g of THF, and the reaction solution is stirred for a further 2 hours in total. The batch is then evaporated in a rotary evaporator, the residue is taken up in 80 ml of methanol, and 11.7 ml of 37% HCl are added. The reaction is warmed to 62°–64° C. in 25 minutes and stirred for a further 40 minutes. The reaction solution is concentrated in a rotary evaporator, added dropwise at about 55° C. to 36 g of demineralised water, and 9.54 ml of 37% HCl are added. The two-phase mixture is stirred at about 62° C. for 75 minutes and subsequently for 16 hours with cooling to RT. The residual THF is stripped off in a rotary evaporator, 50 g of toluene are added, and the pH is adjusted to pH 6.5–7 using about 8 ml of 32% NaOH. The phases are separated, the aqueous phase is post-extracted with 20 ml of toluene, and the organic extracts are evaporated in a rotary evaporator. The residue is chromatographed over 300 g of silica gel with toluene/ethyl acetate 7:3.

Yield: 2.3 g (49%)

(3aS,6aR)- to (3aR,6aS)-lactone=85:15 (HPLC)

Example 3

(−)-Quinine as Chiral Auxiliary Reagent

Example 3A—Solvent THF 5 g (14.865 mmol) of anhydride are suspended in 40 g of THF. A solution of 5.12 g (15.6 mmol; 105 mol %) of (−)-quinine in 14 g of THF is added dropwise at 23°–26° C. over the course of 3 hours. After the mixture has been stirred at RT for 2 hours, the solution is evaporated to dryness in a rotary evaporator.

(4S,5R)- to (4R,5S)-monoester=73:27 (HPLC)

Example 3B—Solvent Toluene 5 g (14.865 mmol) of anhydride are suspended in 50 g of toluene. A solution of 5.12 g (15.6 mmol; 105 mol %) of (−)-quinine in 19 g of toluene is added dropwise at 23°–26° C. over the course of 3 hours. After the mixture has been stirred at RT for 2 hours, the solution is evaporated to dryness in a rotary evaporator.

(4S,5R)- to (4R,5S)-monoester=75:25 (HPLC)

The solution of the product in 20 g of THF is added dropwise to a suspension of 1.67 g (42.4 mmol: 300 mol %)

of sodium borohydride in 30 g of THF, and the reaction is subsequently warmed to 62°–64° C. in 30 minutes and stirred for 90 minutes. The batch is then evaporated in a rotary evaporator, the residue is taken up in 80 ml of methanol, and 10.2 ml of 37% HCl are added. The reaction is warmed to 62°–64° C. in 20 minutes, stirred at this temperature for a further 70 minutes and stirred for a further 14 hours with cooling to RT. The reaction solution is evaporated in a rotary evaporator, and the residue is partitioned between 100 g of demineralised water and 50 g of toluene. The organic extracts are evaporated in a rotary evaporator, and the residue is chromatographed over 200 g of silica gel with toluene/ethyl acetate 7:3.

Yield: 2.2 g (48.7%)

Optical rotation $[\alpha]_{365}^{20}$=+96° (c=1 in benzene). (3aS, 6aR)- to (3aR,6aS)-lactone=74:26 (HPLC)

Example 4

(1S,2R)-(–)-2-(N,N-Di-n-butylamino)-1-phenyl-1-propanol
As Chiral Auxiliary Reagent, Solvent Toluene 5 g (14.865 mmol) of anhydride are suspended in 50 g of toluene. A solution of 4.11 g (15.6 mmol; 105 mol %) of (1S,2R)-(–)-2-(dibutylamino)-phenyl-1-propanol in 19 g of toluene is added dropwise at 23°–26° C. over the course of 3 hours. After the mixture has been stirred at RT for 2 hours, the solution is evaporated to dryness in a rotary evaporator.

(4S,5R)- to (4R,5S)-monoester=27:73 (HPLC)

The solution of the crude product in 30 g of THF and 2.48 g of methanol is added dropwise over the course of 2 hours at 63°–64° C. to a suspension of 1.52 g (38.6 mmol; 261 mol %) of sodium borohydride in 20 g of THF, and the reaction solution is stirred for a further 3 hours in total. The reaction solution is concentrated in a rotary evaporator, added dropwise at about 57° C. to 36 g of demineralised water, and 9.52 ml of 37% HCl are added. The two-phase mixture is stirred at about 62° C. for 75 minutes and subsequently for 16 hours with cooling to RT. The residual THF is stripped off in a rotary evaporator, 50 g of toluene are added, and the pH is adjusted to pH 7.0–7.5 using about 8 ml of 32% NaOH. The phases are separated, the aqueous phase is post-extracted with 20 ml of toluene, and the organic extracts are evaporated in a rotary evaporator. The residue is chromatographed over 300 g of silica gel with toluene/ethyl acetate 7:3.

Yield: 1.78 g (37%)

(3aS,6aR)- to (3aR,6aS)-lactone=25:75 (HPLC)

Example 5

(+)-Cinchonine
As Chiral Auxiliary Reagent, Solvent Toluene 5 g (14.865 mmol) of anhydride are suspended in 50 g of toluene. A solution of 4.65 g (15.6 mmol; 105 mol %) of (+)-cinchonine in 19 g of toluene is added dropwise at 23°–26° C. over the course of 3 hours. After the mixture has been stirred at RT for 2 hours, the solution is evaporated to dryness in a rotary evaporator.

(4S,5R)- to (4R,5S)-monoester=14:86 (HPLC)

The solution of the crude product in 30 g of THF and 2.48 g of methanol is added dropwise over the course of 2 hours at 63°–64° C. to a suspension of 1.52 g (38.6 mmol; 261 mol %) of sodium borohydride in 20 g of THF, and the reaction solution is stirred for a further 3 hours in total. The reaction solution is concentrated in a rotary evaporator, added dropwise at about 58° C. to 36 g of demineralised water, and 9.52 ml of 37% HCl are added. The two-phase mixture is stirred at about 62° C. for 75 minutes and subsequently for 16 hours with cooling to RT. The residual THF is stripped off in a rotary evaporator, 50 g of toluene are added, and the pH is adjusted to pH 7.0–7.5 using about 8 ml of 32% NaOH. The phases are separated, the aqueous phase is post-extracted with 20 ml of toluene, and the organic extracts are evaporated in a rotary evaporator. The residue is chromatographed over 300 g of silica gel with toluene/ethyl acetate 7:3.

Yield: 2.6 g (56%)

(3aS,6aR)- to (3aR,6aS)-lactone 13:87 (HPLC)

Example 6

(–)-Cinchonidine
As Chiral Auxiliary Reagent, Solvent Toluene 5 g (14.865 mmol) of anhydride are suspended in 69 g of toluene. 4.64 g (15.6 mmol; 105 mol %) of (–)-cinchonidine are added in portions at 23° C.–26° C. over the course of 5 hours. After the mixture has been stirred at room temperature [RT] for 65 hours, the precipitate is isolated from the reaction solution.

Yield: 8.1 g (85.9%)

(4S,5R)- to (4R,5S)-monoester=99:1 (HPLC).

The solution still contains residues of the starting materials and the diastereomeric monoesters in a ratio of 5:95.

Example 7 trans-1-Hydroxy-2-pyrrolidinylcyclohexane
As Chiral Auxiliary Reagent, Solvent Toluene 5 g (14.865 mmol) of anhydride are suspended in 50 g of toluene. A solution of 2.64 g (15.6 mmol; 105 mol %) of trans-1-hydroxy-2-pyrrolidinylcyclohexane in 19 g of toluene is added dropwise at 24° C.–26° C. over the course of 1.5 hours. After the mixture has been stirred at room temperature [RT] for 5 hours, the precipitate is isolated from the reaction solution.

Yield: 6.5 g (86.3%)

(4S,5R)- to (4R,5S)-monoester=73:27 (HPLC).

The solution still contains residues of the starting materials and the diastereomeric monoesters in a ratio of 1:1.

What is claimed is:

1. A process for the selective cleavage of a cycloanhydride of the formula I

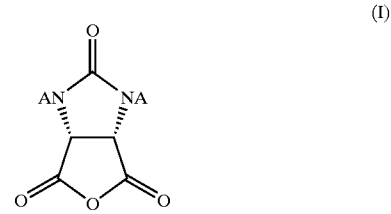

(I)

in which

A is benzyl, alkyl having from 1 to 6 carbon atoms or aryl, to give a corresponding monoester, comprising reacting the compound of the formula I a) with a chiral aminoalcohol of the general formula II

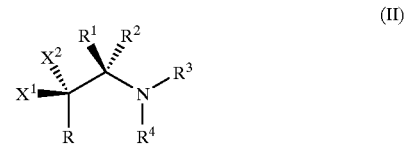

(II)

in which $X^1$ and $X^2$ are each R or OH, with the proviso that $X^1$ is not the same as $X^2$, and one of the two radicals is OH, R, R¹ and R² are each, independently, H, alkyl having 1–12 carbon atoms, unsubstituted or substituted cycloalkyl having 3–8 carbon atoms, alkenyl, aryl, or arylalkyl, and where the substituents may be alkyl, alkenyl, alkoxy, aryl, aryloxy, or dialkylamine with the proviso that at least one of the radicals R, R¹ and R² is an unsubstituted or substituted cycloalkyl, or alkenyl, R³ and R⁴ are each alkyl having 1–12 carbon atoms, unsubstituted or substituted cycloalkyl having 3–8 carbon atoms, alkenyl, aryl, or arylalkyl, with the possible substituents described for R, in an inert solvent, or b) with a chiral aminoalcohol of the general formula III

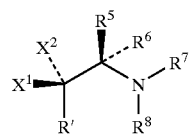
(III)

in which

X¹ and X² are each R' or OH, with the proviso that X¹ is not the same as X², and one of the two radicals is OH, R', R⁵ and R⁶ are each H, alkyl having 1–12 carbon atoms or aryl, which may be substituted by alkyl or alkoxy, and R⁷ and R⁸ are each alkyl having 1–12 carbon atoms or aryl, which may be substituted by alkyl or alkoxy, in toluene, benzene or xylene at a temperature of from 15° to 35° C., in high selectivity to give a diastereomer, and optionally subsequently reducing the monoester using boron hydride, and then closing the ring to give the corresponding lactone.

2. A process according to claim 1, wherein in both variants a) and b), the anhydride is initially introduced in a solvent, and the corresponding aminoalcohol, dissolved in the same solvent, is added.

3. A process according to claim 1, wherein the chiral aminoalcohol used is (+)-N-methylephedrine, (−)-N-methylephedrine, or (1R,2S)-(−)-2-(N,N-di-n-butyl)amino-1-phenyl-1-propanol.

4. A process according to claim 1, wherein the variant a) is carried out at a temperature between 0° C. and the boiling point of the solvent employed.

5. A process according to claim 1, wherein the solvent in variant a) is tetrahydrofuran, toluene or benzene.

6. A process according to claim 1, wherein R¹ and R² are, independently, H or a straight-chain alkyl having 1–4 carbon atoms; and R³ and R⁴ are, independently, a straight-chain alkyl having 1–4 carbon atoms.

7. A process according to claim 6, wherein R of the formula II is an aryl optionally substituted with an alkyl, an alkenyl, an alkoxy, an aryl, an aryloxy, or a dialkylamine.

8. A process for the selective cleavage of a cycloanhydride of the formula I

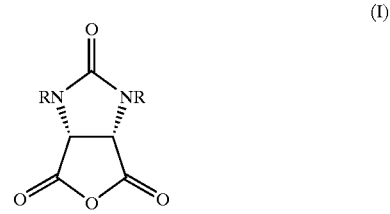
(I)

wherein

R is benzyl, alkyl having from 1 to 6 carbon atoms or aryl, to give a corresponding monoester, comprising reacting a compound of the formula I b) with a chiral aminoalcohol of the general formula III

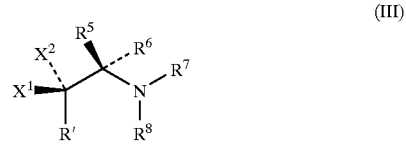
(III)

wherein

X¹ and X² are each R' or OH, with the proviso that X¹ is not the same as X², and one of the two radicals is OH, R', R⁵ and R⁶ are each, independently, H, alkyl having 1–12 carbon atoms or aryl, which may be substituted by alkyl or alkoxy, and R⁷ and R⁸ are each, independently, alkyl having 1–12 carbon atoms or aryl, which may be substituted by alkyl or alkoxy, in toluene, benzene or xylene at a temperature of 15°–35° C., in high selectivity to give a diastereomer, and optionally subsequently reducing the monoester using boron hydride, and then closing the ring to give the corresponding lactone.

9. A process according to claim 1, wherein R of the formula II is aryl, and R¹ and R² are, independently, H or CH₃, and R³ and R⁴ are, independently, CH₃ or C₄H₉.

10. A process according to claim 8, wherein:

R', R⁵ and R⁶ are each, independently, H, alkyl having 1–12 carbon atoms or aryl, which may be substituted by alkyl or alkoxy, and R⁷ and R⁸ are each having 1–12 carbon atoms or aryl, which may be substituted by alkyl or alkoxy.

11. A process according to claim 1, wherein R¹ and R² are H or a straight-chain alkyl having 1–4 carbon atoms; and R³ and R⁴ are a straight-chain alkyl having 1–4 carbon atoms.

12. A process according to claim 11, wherein R of the formula II is an aryl optionally substituted with an alkyl, an alkenyl, an alkoxy, an aryl, an aryloxy, or a dialkylamine.

* * * * *